(12) United States Patent
Di Carlo et al.

(10) Patent No.: US 10,407,709 B2
(45) Date of Patent: *Sep. 10, 2019

(54) METHOD AND DEVICE FOR ISOLATING CELLS FROM HETEROGENEOUS SOLUTION USING MICROFLUIDIC TRAPPING VORTICES

(71) Applicant: THE REGENTS OF THE UNIVERSITY OF CALIFORNIA, Oakland, CA (US)

(72) Inventors: Dino Di Carlo, Los Angeles, CA (US); Soojung C. Hur, Boston, MA (US); Albert J. Mach, San Jose, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 680 days.

This patent is subject to a terminal disclaimer.

(21) Appl. No.: 14/819,302

(22) Filed: Aug. 5, 2015

(65) Prior Publication Data

US 2015/0355060 A1 Dec. 10, 2015

Related U.S. Application Data

(62) Division of application No. 13/823,112, filed as application No. PCT/US2011/051224 on Sep. 12, 2011, now Pat. No. 9,133,499.

(60) Provisional application No. 61/382,840, filed on Sep. 14, 2010.

(51) Int. Cl.
| | |
|---|---|
| C12Q 1/24 | (2006.01) |
| G01N 1/40 | (2006.01) |
| B01L 3/00 | (2006.01) |
| C12M 1/00 | (2006.01) |
| C12M 3/06 | (2006.01) |
| G01N 33/58 | (2006.01) |
| G01N 33/50 | (2006.01) |
| C12Q 1/68 | (2018.01) |

(52) U.S. Cl.
CPC .......... *C12Q 1/24* (2013.01); *B01L 3/502746* (2013.01); *B01L 3/502761* (2013.01); *C12M 23/16* (2013.01); *C12M 29/00* (2013.01); *C12M 47/04* (2013.01); *C12Q 1/68* (2013.01); *G01N 1/4077* (2013.01); *G01N 33/5091* (2013.01); *G01N 33/582* (2013.01); *B01L 2200/0668* (2013.01); *B01L 2300/087* (2013.01); *B01L 2300/0816* (2013.01); *B01L 2300/0864* (2013.01); *B01L 2300/0867* (2013.01); *B01L 2400/0487* (2013.01); *B01L 2400/082* (2013.01); *B01L 2400/086* (2013.01); *G01N 1/40* (2013.01)

(58) Field of Classification Search
None
See application file for complete search history.

(56) References Cited

U.S. PATENT DOCUMENTS

| | | |
|---|---|---|
| 7,803,599 B2 | 9/2010 | Lutz et al. |
| 9,005,455 B2 | 4/2015 | Achard et al. |
| 9,133,499 B2 | 9/2015 | Di Carlo et al. |
| 2005/0048581 A1 | 3/2005 | Chiu et al. |
| 2008/0009780 A1 | 1/2008 | Leonard |
| 2008/0318324 A1 | 12/2008 | Chiu et al. |
| 2009/0014360 A1 | 1/2009 | Toner et al. |
| 2009/0286300 A1 | 11/2009 | Le Vot et al. |
| 2010/0247492 A1 | 9/2010 | Kuhn et al. |
| 2010/0279321 A1 | 11/2010 | Chin et al. |
| 2011/0070581 A1 | 3/2011 | Gupta et al. |
| 2011/0096327 A1 | 4/2011 | Papautsky et al. |
| 2011/0117577 A1 | 5/2011 | Reboud et al. |
| 2016/0139015 A1 | 5/2016 | Di Carlo et al. |
| 2017/0114385 A1 | 4/2017 | Di Carlo |

FOREIGN PATENT DOCUMENTS

| | | |
|---|---|---|
| EP | 2616551 | 5/2016 |
| WO | WO 02/092222 A2 | 11/2002 |
| WO | WO 2008/157257 A1 | 12/2008 |
| WO | WO 20101036912 A2 | 4/2010 |
| WO | 2012/037030 | 3/2012 |

OTHER PUBLICATIONS

Gossett et al. 2010. Label-free cell separation and sorting in microfluidic systems Analytical and Bioanalytical Chemistry, vol. 397, pp. 3249-3267.*
Park et al., Continuous focusing of microparticles using inertial lift force and vorticity via multi-orifice microfluidic channels, Lab Chip, 2009, 9 939-948.*
Pamme, Continuous flow separations in microfluidic devices, Lab Chip, 2007, 7, 1644-1659.*
Takagi et al., Continuous particle separation in a microchannel having asymmetrically arranged multiple branches, Lab Chip, 2005, 5, 778-784.*
Bhagat, Ali Asgar S. et al., Pinched flow coupled shear-modulated inertial microfluidics for high-throughput rare blood cell separation, Lab Chip, 2011, 11, 1870-1878.

(Continued)

*Primary Examiner* — Louise W Humphrey
*Assistant Examiner* — Srikanth Patury
(74) *Attorney, Agent, or Firm* — Vista IP Law Group LLP

(57) ABSTRACT

A method of isolating cells includes providing a microfluidic device having at least one microfluidic channel coupled to an inlet and an outlet, the at least one microfluidic channel comprises at least one expansion region disposed along the length thereof. The at least one expansion region is an abrupt increase in a cross-sectional dimension of the at least one microfluidic channel configured to generate a vortex within the at least one expansion region in response to fluid flow. A solution containing a population of cells at least some of which have diameters ≥10 μm flows into the inlet. A portion of cells is trapped within vortex created within the at least one expansion region. The trapped cells may then released from the expansion region.

9 Claims, 16 Drawing Sheets

(56) References Cited

OTHER PUBLICATIONS

Cristofanilli, Massimo et al., Circulating Tumor Cells: A Novel Prognostic Factor for Newly Diagnosed Metastatic Breast Cancer, Journal of Clinical Oncology, vol. 23, No. 7 (Mar. 1, 2005), pp. 1420-1430.
Lin, Cheng Ming et al., Trapping of Bioparticles via Microvortices in a Microfluidic Device for Bioassay Applications, Anal. Chem. 2008, 80 (23), pp. 8937-8945.
Nagrath, Sunitha et al., Isolation of rare circulating tumour cells in cancer patients by microchip technology, Nature 450, 1235-1239 (Dec. 20, 2007).
Moon, Hui-Sung et al., Continuous separation of breast cancer cells from blood samples using multi-orifice flow fractionation (MOFF) and dielectrophoresis (DEP), Lab Chip, 2011, 11, 1118-1125.
Park, Jae-Sung et al., Continuous focusing of microparticles using inertial lift force and vorticity via multi-orifice microfluidic channels, Lab Chip, 2009, 9, 939-948.
Stott, Shannon L. et al., Isolation of circulating tumor cells using a microvortex-generating herringbone-chip, Center of Engineering in Medicine, Massachusetts General Hospital, Harvard Medical School, Boston, MA 02114, USA, PNAS, Oct. 26, 2010, vol. 107, No. 43, pp. 18392-18397.
Sethu, Palaniappan et al., Microfluidic Isolation of Leukocytes from Whole Blood for Phenotype and Gene Expression Analysis, Anal. Chem., 2006, 78(15), pp. 5453-5461.
Hur, Soojung Claire et al., High-throughput size-based rare cell enrichment using microscale vortices, Biomicrofluidics, vol. 5(2), pp. 22206-01-22206-10 (Jun. 29, 2011).
Mach, Albert J. et al., Continuous Scalable Blood Filtration Device Using Inertial Microfluidics, Biotechnology and Bioengineering, vol. 107, No. 2, Oct. 1, 2010, pp. 301-311.
Park, Jae-Sung et al., Multiorifice Flow Fractionation: Continuous Size-Based Separation of Microspheres Using a Series of Contraction/Expansion Microchannels, Anal. Chem. 2009, 81, pp. 8280-8288.
PCT International Search Report for PCT/US2011/051224, Applicant: The Regents of the University of California, Form PCT/ISA/210 and 220, dated Apr. 18, 2012 (4pages).
PCT Written Opinion of the International Search Authority for PCT/US2011/051224, Applicant: The Regents of the University of California, Form PCT/ISA/237, dated Apr. 18, 2012 (4pages).
PCT International Preliminary Report on Patentability (Chapter I of the Patent Cooperation Treaty) for PCT/US2011/051224, Applicant: The Regents of the University of California, Form PCT/IB/326 and 373, dated Mar. 28, 2013 (6pages).
Patent Examination Report No. 1, dated Jul. 15, 2014, in Australian Patent Application No. 2011302302, Application: The Regents of the University of California (10pages).
Chiu, D.T., Cellular manipulations in microvortices, Anal Bioanal Chem (2007) 387:17-20.
Khabiry, M. et al., Cell Docking in Double Grooves in a Microfluidic Channel, NIH Public Access Author Manuscript, 2009, [Retrieved on Feb. 13, 2014]. Retrieved from the Internet <URL:http://www.ncbi.nih.gov/pmc/articles/PMC2683980/> published in final edited form as: Small, 5(10):1186-1194.
Lee, M.G. et al., Three-dimensional hydrodynamic focusing with a single sheath flow in a single-layer microfluidic device, Lab on a Chip, 2009, 9(21):3155-3160.
Lettieri, G.L, et al., A novel microfluidic concept for bioanalysis using freely moving beads trapped in recirculating flows, Lab on a Chip, 2003, 3(1):34-39.
Shelby, J.P., et al, High radial acceleration in microvortices, Nature, 2003, 425:38.
Notification of the First Office Action including an English translations prepared by Kangxin Partners, P.C.dated Feb. 17, 2014, in Chinese Patent Application No. 201180044092.8 Application: The Regents of the University of California (16pages).

Notification of the Second Office Action including an English translations prepared by Kangxin Partners, P.C. dated Aug. 5, 2014, in Chinese Patent Application No. 201180044092.8 Application: The Regents of the University of California (8pages).
Karino et al., 1977. Flow Behaviour of Blood Cells and Rigid Spheres in an Annular Vortex. Philosophical Transactions of the Royal Society of London. Series B, Biological Sciences, vol. 279, No. 967, pp. 413-445.
Gossett et al. 2010. Label-free cell separation and sorting in microfluidic systems. Analytical and Bioanalytical Chemistry, vol. 397, pp. 3249-3267.
Bergman et al. 1995-2006. Anatomy Atlases, A digital library of anatomy information, 9 pages.
Hsu et al. 2008. Microvortex for focusing, guiding and sorting of particles. Lab on a Chip, vol. 8, pp. 2128-2134.
Sollier, Elodie et al., Passive microfluidic devices for plasma extraction from whole human blood, Sens. Actuators B: Chem. (2009), doi:10.1016/j.snb.2009.05.023.
Sollier, Elodie et al., Fast and continuous plasma extraction from the whole human blood based on expanding cell-tree layer devices, Biomed Microdevices (2010) 12:485-497.
Notice of Rejection dated Sep. 29, 2015 in Japanese Patent Application No. 2013-528369, Applicant: The Regents of the University of California, (3pges).
First Office Action dated Jan. 19, 2016 in Chinese Patent Application No. 2015100887109, Applicant: The Regents of the University of California, (16pgs).
Extended European Search Report (EESR) dated Apr. 4, 2016 in European Patent Application No. 11825738.5, Applicant: The Regents of the University of California, (7pgs).
Patent Examination Report No. 1 dated Jan. 15, 2016 in Australian Patent Application No. 2015200910, Applicant: The Regents of the University of California, (5pgs).
Patent Examination Report No. 2 dated Apr. 4, 2016 in Australian Patent Application No. 2015200910, Applicant: The Regents of the University of California, (3pgs).
Notice of Acceptance dated Sep. 7, 2016 in Australian Patent Application No. 2015200910, Applicant: The Regents of the University of California, (1pg).
Communication pursuant to Article 94(4) EPC dated Nov. 23, 2016 in European Application No. 11 825 738.5-1371, Applicant: The Regents of the University of California (3pages).
Examiner's Report dated Sep. 27, 2017 in Canadian Patent Application No. 2,809,877, (7pages).
Office Action dated Sep. 7, 2017 in U.S. Appl. No. 14/948,119, (33pages).
Chiou et al. (2005. Massively parallel manipulation of single cells and microparticles using optical images. Nature 436, pp. 370-372.
Notice of Acceptance dated Nov. 26, 2014 in Australian Patent Application No. 2011302302, Applicant: The Regents of the University of California (3pages).
Communication pursuant to Article 94(3) EPC, dated Jul. 17, 2018 in European Patent Application No. 11825738.5-1101, (3pages).
Restriction Requirement dated Aug. 8, 2018 in U.S. Appl. No. 15/345,359, (11pages).
Park, Jae-Sung et al., Multiorifice Flow Fractionation: Continuous Size-Based Separation of Microsphere Using a Series of Contraction/Expansion Microchannels, Anal. Chem. 2009, 81, 8280-8288.
Philosophical Transactions of the Royal Society of London, Flow Behaviour of Blood Cells and Rigid Spheres in an Annular Vortex, B. Biological Sciences, vol. 279, No. 967, pp. 413-445.
Office Action dated Jan. 7, 2019 for U.S. Appl. No. 15/345,359, filed Nov. 7, 2016, Inventor: Dino Di Carlo, (7pages).
Third Examination Report dated Dec. 21, 2018 for European Patent Application No. 11825738.5, (4pages).
Office Action dated Sep. 25, 2018 for Canadian Patent Application No. 2809877, (3pages).

* cited by examiner

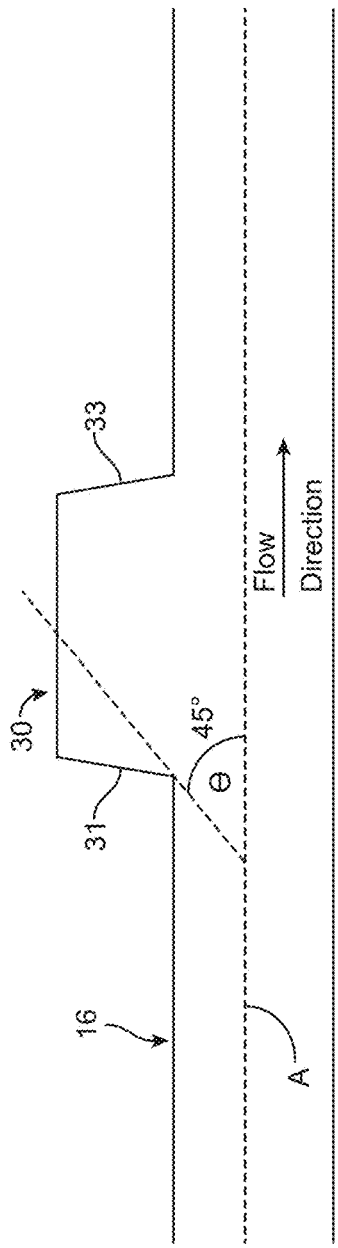
FIG. 1C
FIG. 1D
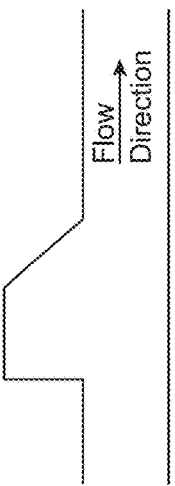
FIG. 1E
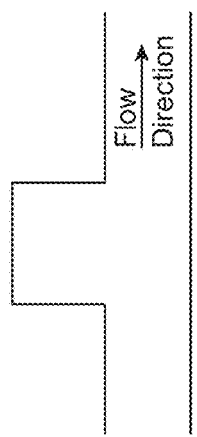
FIG. 1F
FIG. 1G

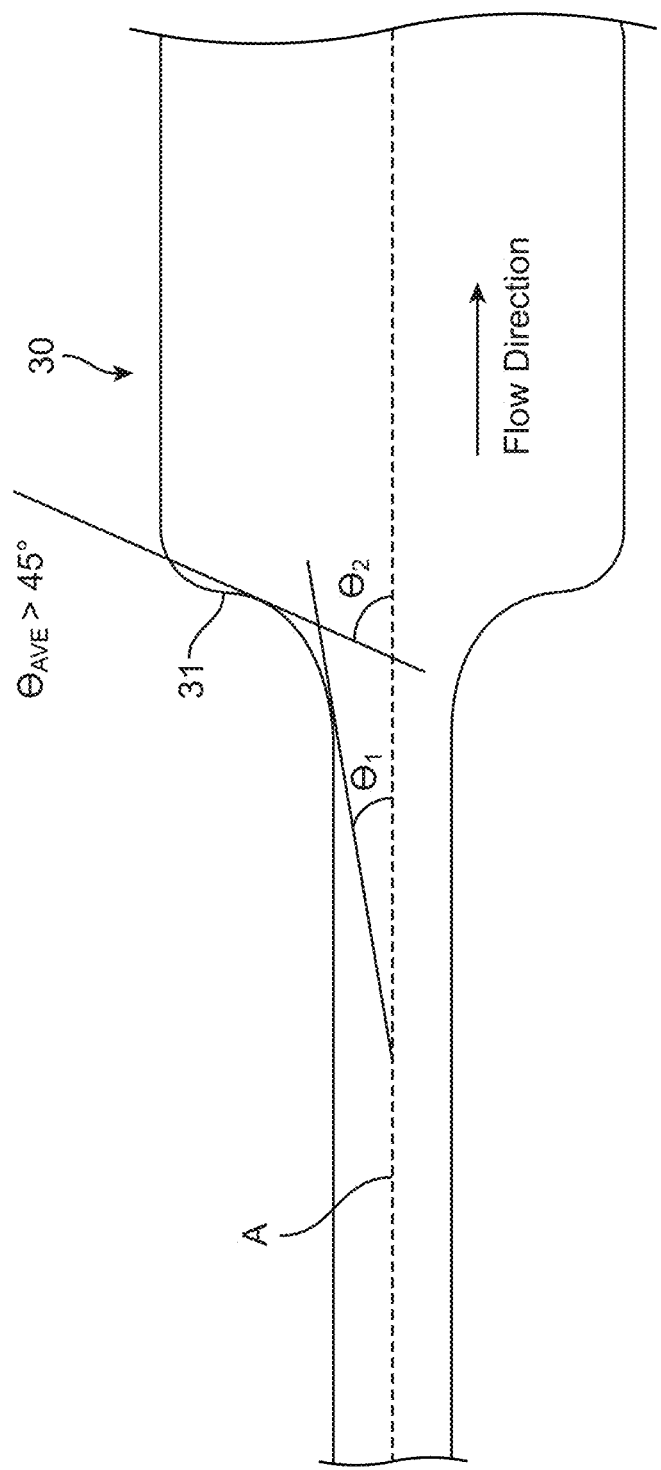

Flow direction ⇒

1. Capture (Øs)

Blood Cells

2. Blood Cell Flush (9s)

No Blood Cells

3. Trapped Cell Release (17s)

4. Complete Release (18s)

200μm

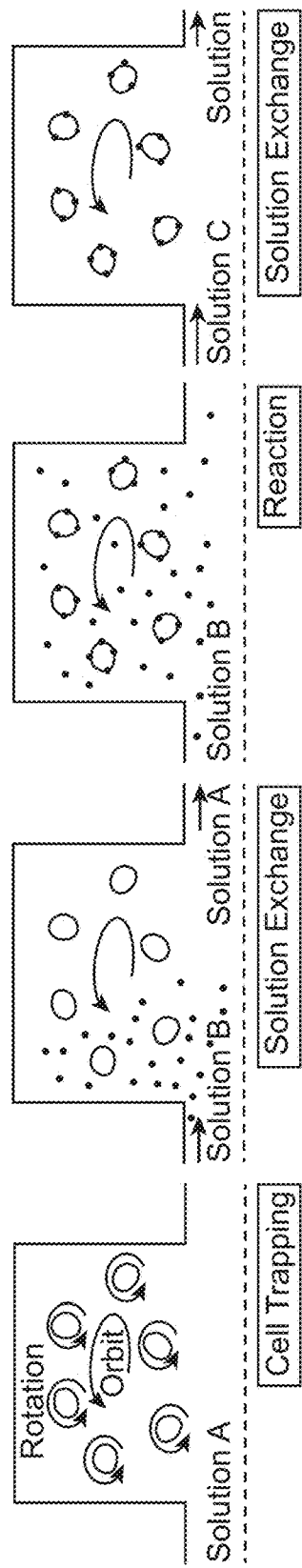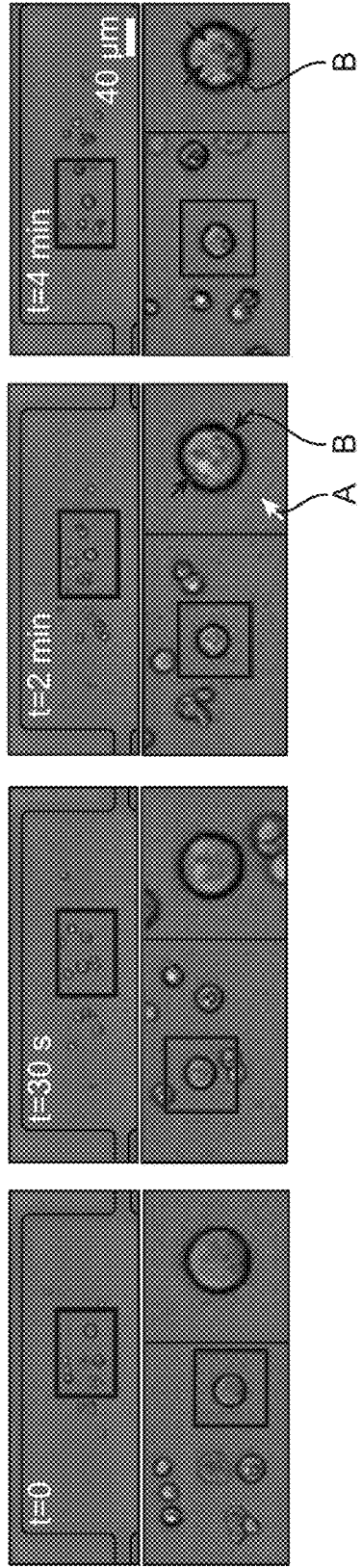
FIG. 6A  FIG. 6B  FIG. 6C  FIG. 6D
FIG. 6E  FIG. 6F  FIG. 6G  FIG. 6H

METHOD AND DEVICE FOR ISOLATING CELLS FROM HETEROGENEOUS SOLUTION USING MICROFLUIDIC TRAPPING VORTICES

RELATED APPLICATIONS DATA

This Application is a divisional of U.S. patent application Ser. No. 13/823,112 filed on Mar. 14, 2013, now issued as U.S. Pat. No. 9,133,499, which is a U.S. National Stage filing under 35 U.S.C. § 371 of International Application No. PCT/US2011/051224, filed Sep. 12, 2011, which claims priority to U.S. Provisional Patent Application No. 61/382,840 filed on Sep. 14, 2010. The contents of the aforementioned applications are hereby incorporated herein by reference in their entirely. Priority to the aforementioned applications are hereby expressly claimed in accordance with 35 U.S.C. §§ 119, 120, 365 and 371 and any other applicable statutes.

FIELD OF THE INVENTION

The field of the invention generally relates to microfluidic devices and methods for the isolation and sorting of cells or particles. More particularly, the field of the invention pertains to microfluidic devices and methods that utilize microfluidic trapping vortices for isolating cells or particles from a heterogeneous solution.

BACKGROUND

The standard benchtop centrifuge is one of the most common instruments in the life science laboratory used ubiquitously for sample preparation in cell biology research and medical diagnostics. Typical sample preparation procedures require multiple centrifugation steps for cell labeling and washing, which can be a time consuming, laborious, and costly process for diagnostics and research. In fact, while assays themselves have widely been miniaturized and automated, sample preparation required for these assays has been identified as a key target for future automation.

Centrifuges perform three critical sample preparation steps that make them so widely used: (i) separation of cells by size/density, (ii) concentration of cells, and (iii) solution exchange. Because centrifuges can perform such disparate functions, realizing these functions in a miniaturized platform has been challenging. Miniaturized microfluidic approaches often successfully implement one or two of these functions. For example, cell separation by size and density has been accomplished by using physical obstacles, external forces, or fluidic forces to guide particles to defined locations in a microchannel for collection at different outlets. While these methods may offer high resolution cell separation, the typical collected liquid volume is similar to the injected liquid volume—that is, no significant concentration is achieved. This large output volume can hinder downstream cell detection platforms that may require scanning large fields of view to observe the cells of interest or leads to dilution of biomolecules of interest if collected cells must be lysed. Thus, a method of concentration must be used in-line with the separation system to reduce the liquid volume for rapid detection and analysis.

There are a variety of techniques for concentrating particles and cells in localized regions with microfluidic systems. Of these, mechanical traps are the most commonly used method that anchors particles and cells to a physical structure and enables multistep perfusion of reagents to perform cell assays on-chip via solution exchange. Often, however, it may be important to release particles and cells on-demand for further downstream analysis. Although successful at concentration and release, cells immobilized in these trap-and-release systems can squeeze through traps and become damaged when operated at higher volumetric throughput, thereby limiting concentration factors to below what is necessary for concentration of rare cells or dilute cell solutions. Thus, a general purpose miniaturized tool that recapitulates all of the functions and flexibility of a traditional centrifuge has yet to be achieved.

The formation of vortices within a microfluidic structure has been used for focusing and filtration enhancement. For example, Park et al. (Jae-Sung et al., Continuous focusing of microparticles using inertial lift force and vorticity via multi-orifice microfluidic channels, Lab Chip, 9, 939-948 (2009)) discloses a microfluidic device used in experiments that focuses rigid microparticles using a series of suddenly expanding and contracting channels. At certain flow rates, vortices are formed within the expanded channels. The vortices formed within the expanded channels induce lateral particles migration like a tubular pinch effect. By having a series of these expanded channels along a length of a microchannel, rigid microparticles are able to gradually migrate (i.e., are focused) to opposing sides of the microchannel. Importantly, however, the expanded channels do not trap the particles. Instead, Park et al. discloses a structure that continuously focuses microparticles passing through the device. In Park et al., small diameter (7 μm diameter) polystyrene microspheres were run through a multi-orifice microchannel and trapping of these particles was not observed. Park et al. further observed that larger-sized particles tended to move away from the expanding channel regions where vortices were formed. Park et al. also discloses that particles in the sample should be like rigid spheres for maximal value of the inertial lift force which obviously runs counter to its use with living cells that, by their nature, are generally deformable. Structurally, Park et al. discloses rather small-sized expanding channels that expand outward a distance of around 80 μm with respect to the upstream contracting channel. Further, the length of the expanding channels is also small, disclosed as being 200 μm.

U.S. Patent Application No. 2008/0318324 (Chiu et al.) discloses a biochip for the high-throughput screening of cancer cells. The device uses effusive filtration to segregate tumor cells from a sample of bodily fluid. Effusive filtration refers to filtration configurations where the fluid is dispersed or redistributed by the filtration media or any morphological features inside the flow channel. In Chiu et al., the filtration media are side wall apertures having a width smaller than that of the cell. In one embodiment, Chiu et al. discloses a 1-D channel having an expansion and constriction point to either slow down or speed up flow. Chiu et al. discloses that at high velocities the fluid may become separated to form internal microvortices which aid in the filtration operation by altering fluid flow dynamics. The microvortices, however, do not trap cells passing through the device. Rather, the apertures that line sections of the channel retain larger-sized cells by preventing the same from passing there through. While structures are disclosed that generate vortices for focusing or filtration aiding purposes, these structures are not used to selectively trap cells therein.

SUMMARY

In one embodiment of the invention, a method of isolating cells includes providing a microfluidic device having at least one microfluidic channel coupled to an inlet and an outlet, the at least one microfluidic channel comprising at least one expansion region disposed along the length thereof, the at least one expansion region comprising an abrupt increase in a cross-sectional dimension of the at least one microfluidic channel configured to generate a vortex within the at least one expansion region in response to fluid flow. A solution containing a population of cells is flowed into the inlet. At least some of the cells are trapped within the vortex created within the at least one expansion region, the at least some of the cells having diameters ≥10 µm. The trapped cells are released from the plurality expansion regions by reducing the flow rate of solution through the at least one microfluidic channel.

In another embodiment of the invention, a method of exchanging solution around isolated cells includes providing a microfluidic device having at least one microfluidic channel coupled to an inlet and an outlet, the at least one microfluidic channel comprising at least one expansion region disposed along the length thereof, the at least one expansion region comprising an abrupt increase in a cross-sectional dimension of the at least one microfluidic channel configured to generate a vortex within the at least one expansion region in response to fluid flow. A first solution containing a population of cells is flowed into the inlet. At least a portion of the cells are trapped within the vortex created within the at least one expansion region. One or more solutions different from the first solution are then flowed into the inlet while continuously maintaining the vortex containing the trapped cells.

In another embodiment of the invention, a method of trapping particles or cells by size includes providing a microfluidic device having at least one microfluidic channel coupled to an inlet and an outlet, the at least one microfluidic channel comprising at least one expansion region disposed along the length thereof, the at least one expansion region comprising an abrupt increase in a cross-sectional dimension of the at least one microfluidic channel configured to generate a vortex within the at least one expansion region in response to fluid flow. A solution containing a plurality cells or particles is flowed into the inlet. At least some of the cells or particles are trapped within the vortex created within the at least one expansion region, wherein the cells or particles having a size above threshold value are substantially trapped within the vortex and wherein cells or particles having a size below a threshold value substantially pass by the vortex.

In another embodiment of the invention, a microfluidic device includes a substrate containing at least one microfluidic channel coupled to at least one inlet and an outlet, the at least one microfluidic channel comprising at least one expansion region disposed along the length of the at least one microfluidic channel, the at least one expansion region comprising an abrupt increase of at least 80 µm in a cross-sectional dimension of the at least one microfluidic channel, the at least one expansion region configured to generate a vortex within the at least one expansion region in response to fluid flow.

In another embodiment of the invention, a microfluidic system includes a substrate containing at least one microfluidic channel coupled to at least one inlet and an outlet, the at least one microfluidic channel comprising at least one expansion region disposed along the length of the at least one microfluidic channel, the at least one expansion region comprising an abrupt increase in a cross-sectional dimension of the at least one microfluidic channel configured to generate a vortex within the at least one expansion region in response to fluid flow. The system includes at least one pump configured to pump fluid into the at least one inlet containing particles or cells. A computer is operatively coupled to the at least one pump and configured to adjust the flow rate of fluid passing through the at least one microfluidic channel.

BRIEF DESCRIPTION OF THE DRAWINGS

FIG. 1C illustrates a schematic representation of a microfluidic channel with a single expansion region.

FIGS. 1D-1G illustrate various geometries of the expansion region.

FIG. 1J illustrates a schematic representation of a microfluidic channel with an expansion region according to another aspect of the invention.

FIG. 4C illustrates an image taken at t=0 seconds. FIG. 4D illustrates an image taken at t=9 seconds. FIG. 4E illustrates an image taken at t=17 seconds. FIG. 4F illustrates an image taken at t=18 seconds. HeLa cells are seen trapped within the vortex created within the expansion region.

FIG. 6A illustrates a schematic representation of solution containing MCF7 cells (Solution A) wherein the cells are trapped within a vortex created within an expansion region.

FIG. 6B illustrates a schematic representation of a first solution exchange occurring with Solution B that includes streptavidin-coated microspheres.

FIG. 6C illustrates a schematic representation of the reaction of the MCF7 cells with the streptavidin-coated microspheres.

FIG. 6D illustrates a schematic representation of a second solution exchanged conducted with Solution C (i.e., PBS) that acts as a wash.

FIG. 6E illustrates a microscopic image of MCF7 cells corresponding to FIG. 6A wherein cells orbit within a vortex created within an expansion region of the microfluidic device. Below left is a magnified view of the rectangular region. Below right is a magnified view of the square region.

FIG. 6F illustrates a microscopic image corresponding to FIG. 6B. Below left is a magnified view of the rectangular region. Below right is a magnified view of the square region.

FIG. 6G illustrates a microscopic image corresponding to FIG. 6C. Below left is a magnified view of the rectangular region. Below right is a magnified view of the square region.

FIG. 6H illustrates a microscopic image corresponding to FIG. 6D. Below left is a magnified view of the rectangular region. Below right is a magnified view of the square region.

DETAILED DESCRIPTION OF THE ILLUSTRATED EMBODIMENTS

Figure 1A:
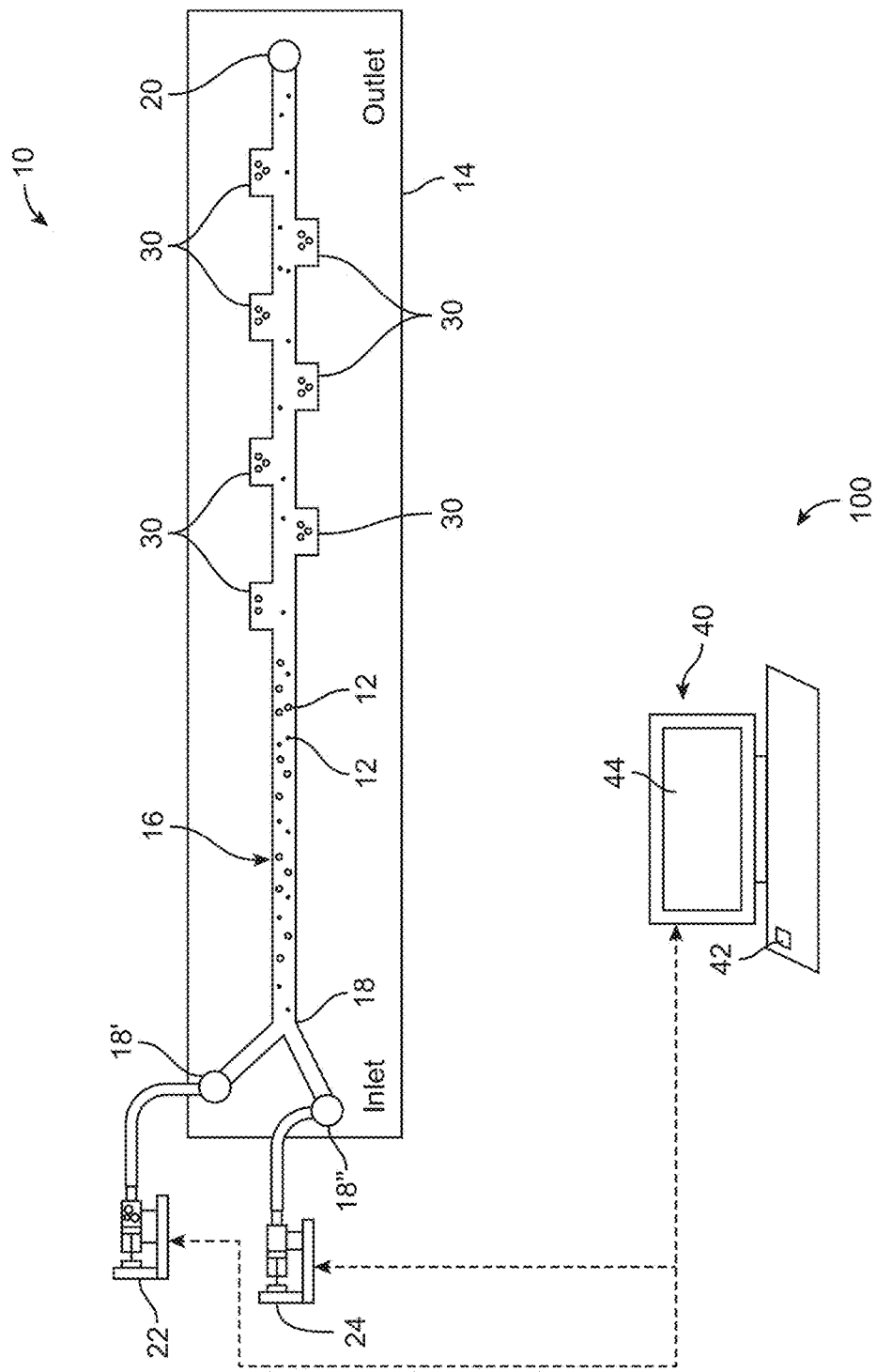
FIG. 1A illustrates a microfluidic system for isolating cells according to one embodiment.

FIG. 1A illustrates a microfluidic device 10 for isolating cells 12 from a heterogeneous solution containing cells 12 of different sizes. While the microfluidic device 10 is illustrated in FIG. 1A as being used for isolating cells 12 it should be understood that the microfluidic device 10 may also be used in connection with the isolation of particles (not shown). Thus, use of the term "cell" or "cells" herein should be interchangeable with particle or particles. As seen in FIG. 1A, the microfluidic device 10 includes a substrate 14 that contains a microfluidic channel 16 coupled to an inlet 18 and an outlet 20. The dimensions of the microfluidic channel 16 may vary. As an example, the microfluidic channel may have a width of 50 μm and a height of 70 μm. Typical dimensions for the width of microfluidic channel 16 are in the range of 20 μm to 200 μm. Typical dimensions for the height of the microfluidic channel 16 are the range of 20 μm to 500 μm. The length may also vary but it generally is several centimeters in length (e.g., 4.5 cm). The substrate 14 may be formed from conventional materials used for microfluidic devices. These include glass, silicon, or polydimethylsiloxane (PDMS). For PDMS, soft lithography techniques may be used to create the microfluidic device 10. In the PDMS embodiment, for mold fabrication, a 4 inch silicon wafer is spin-coated with a 70 μm thick layer of a negative photoresist (KMPR 1050, Microchem), and exposed to UV-light through a designed Cr-photomask and developed. PDMS (Sylgard 184, Dow Corning) was cast on to the prepared mold and degassed. Cured PDMS cast was separated from the mold and the inlet 18 and outlet 20 were punched with a pin vise (Pin vise set A, Technical Innovations Inc.). The now-punched PDMS layer was bonded to a slide glass by exposing both PDMS and a slide glass surfaces to air plasma (Plasma Cleaner, Harrick Plasma) to enclose the device.

In the embodiment of FIG. 1A, the inlet 18 actually includes two inlets—inlet 18' and inlet 18". The first inlet 18' is used to introduce the solution containing the heterogeneous population of cells 12. The second inlet 18" is used to introduce a second, different solution. As explained in more detail below, the second inlet 18" may be used to introduce a wash solution, label (e.g., fluorescent label, antibody, nucleic acid dye, fluorogenic substrate), or other chemical agent (e.g., fixation agent or permeabilization agent) into the microfluidic channel 16.

As seen in FIG. 1A, the inlets 18', 18" are coupled to respective pumps 22, 24. Each pump 22, 24 can be used to deliver a set flow rate of the respective solution to the microfluidic device 10. Any type of pump known to those skilled in the art may be used in connection with the invention. These include, without limitation, syringe pumps, pumps operating on pressurized air to pump fluid, peristaltic or positive displacement pumps. FIG. 1A illustrates syringe pumps 22, 24 used with the microfluidic device 10. For example, a Harvard Apparatus, PHD 2000 syringe pump may be used to sustain an overall flow rate ranging between 10 μl/min and 4.5 ml/min. Typically, the settings of the pumps 22, 24 are set to generate a flow rate through the microfluidic device 10 greater than 100 μl/min.

FIG. 1A illustrates a computer 40 that can be used as part of a system 100 to control the microfluidic device 10. The computer 40 typically contains at least one processor 42 therein that executes software residing in or stored on the computer 40. The computer 40 also may include a monitor 44 that can be used to display various parameters of the microfluidic device 10. These may include, for example, flow rates of pumps 22, 24, volume of fluid contained in pumps 22, 24, and other operational data. The computer 40 preferably interfaces with the pumps 22, 24 such that the computer 40 is able to adjust the individual flow rates or operational states of the pumps 22, 24. The computer 40 may control the pumps 22, 24 automatically using a preset algorithm or set of instructions stored in the computer 40. Alternatively, control of the pumps 22, 24 may be manually adjusted using an interface device commonly used with computers (e.g., keyboard, mouse, etc.)

During solution exchange operations, the computer 40 can ensure that the desired flow of solution of maintained in the microfluidic device 10. For instance, when one pump 22 is slowed or even turned off, the flow rate of the second pump 24 is increased to ensure that the desired flow rate is maintained.

Figure 1B:
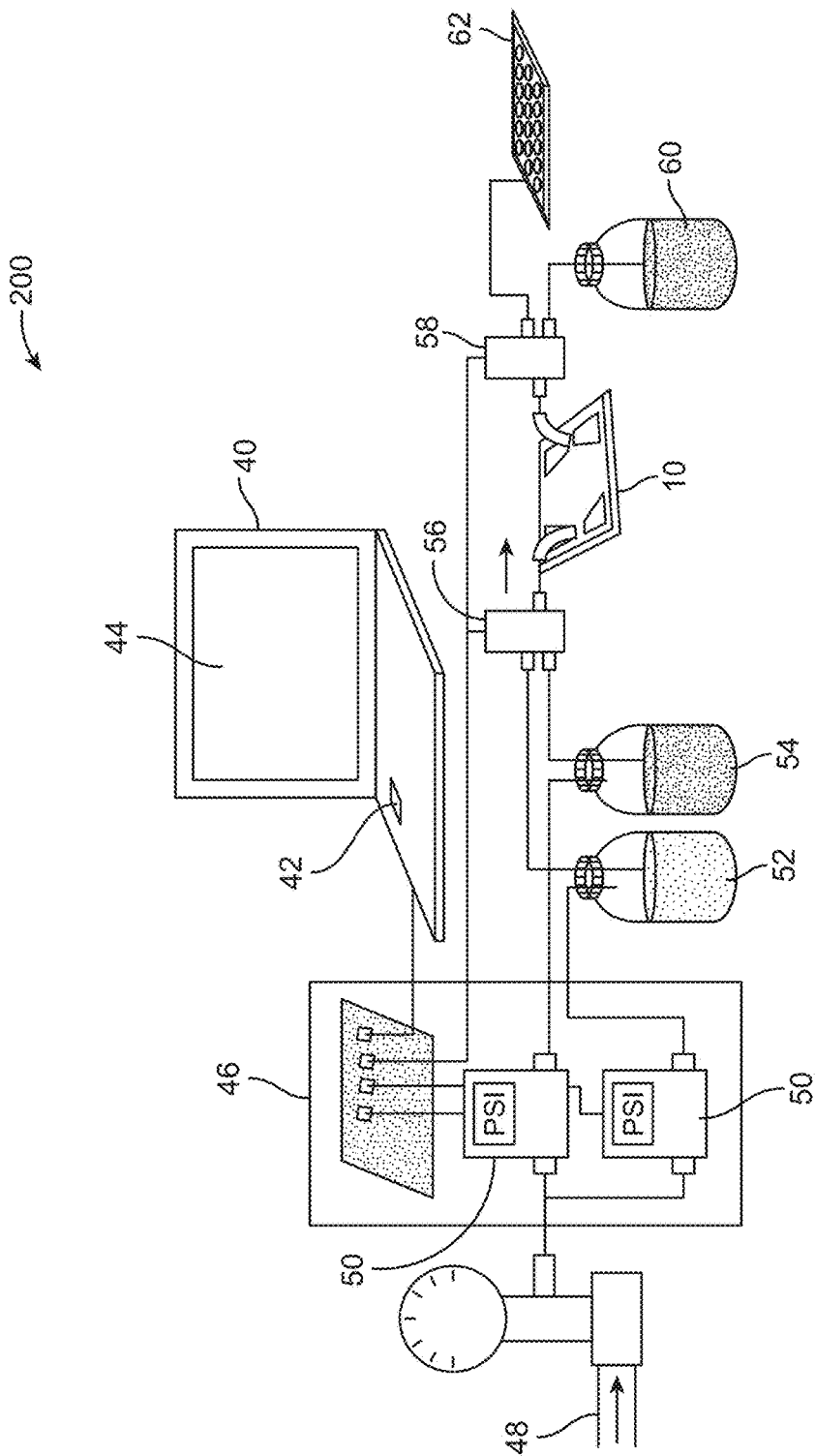
FIG. 1B illustrates a micro system for isolating cells according to another embodiment.

FIG. 1B illustrates an alternative system 200 that uses a pressure driven pumping system 46. The pumping system 46 uses a source of pressurized gas 48 along with regulators 50 to pump a first fluid 52 (e.g., wash) and second fluid 54 (e.g. blood) into the device 10. In this system 200, liquid valves 56, 58 are provided on the input and output, respectively, of the device 10. A computer 40 is configured to control the pressure driven pumping system 46 and the liquid valves 56, 58. For example, valve 56 may be used to open or close flow of either the first fluid 52 or the second fluid 54 to the device 10. Valve 58 can be used to switch outlet flows between a waste receptacle 60 and a collection device 62 which may include, as an example, a 96 well plate.

As seen in FIG. 1A, the microfluidic channel 16 includes a plurality of expansion regions 30 located at selected points along the length of the microfluidic channel 16. The expansion regions 30 provide an abrupt increase in the width of the microfluidic channel 16 that, at or above certain threshold flow rates, create a detached boundary layer that causes the formation of vortices within each expansion region 30. It is the vortices created within the expansion regions 30 that trap a subpopulation of cells 12 from a solution of heterogeneous cells 12 traveling through the microfluidic device 10. These vortices, however, are different from the vortices created in the streamwise direction such as Dean vortices created in curved channel flows with inertia (See J. Wang et al., Vortex-assisted DNA Delivery, Lab Chip, 2010, 10, 2057-2061 (2010)) or vortices created due to asymmetrically structured microchannels (See Stott et al., Isolation of Circulating Tumor Cells Using a Microvortex-Generating Herringbone-Chip, Proc Natl. Acad. Sci. 107(43):18392-7 (2010)). As explained in more detail below, cells 12 above a certain threshold or cutoff size (which depends on the flow rate and geometry of the microfluidic device 10) enter the expansion regions 30 and get caught or trapped within the re-circulating vortices. Cells 12 that are below the threshold size do not get caught and continue to flow downstream in the microfluidic device 10. Generally, the most efficient trapping occurs for cells 12 having diameters greater than 15 µm. At diameters of less than 10 µm, trapping is less efficient (e.g. 5%). Thus, the diameters of the trapped cells 12 should be ≥10 µm in order for meaningful trapping to occur. The geometry of the expansion region 30 may vary. For example, the expansion region 30 can be rectangular as illustrated in FIG. 1A but it may also include a square, triangle, polygonal, or semi-circular profile as illustrated in FIGS. 1C-1G. For rectangular-shaped expansion regions 30 the trapping ability is better with the long side of the expansion region 30 being oriented parallel to the main microfluidic channel 16. Generally, the leading wall 31 (illustrated in FIG. 1C) of the expansion region 30 should be angled at or above 45° with respect to the flow direction of the upstream microfluidic channel 16.

FIG. 1C illustrates a single expansion region 30 along with the upstream microfluidic channel 16. As stated above, the leading wall 31 should be angled at or above 45° with respect to the axis of flow illustrated as dashed line A in FIG. 1C. In this regard, the expansion region 30 is an abrupt expansion in cross-sectional dimension (e.g., width or height) compared to the cross-sectional dimension in the immediately upstream portion of microfluidic channel 16. In the embodiment of FIG. 1C, the leading wall 31 is angled just less than 90° which is well above the minimum 45° threshold value. The expansion region 30 also has a trailing wall 33. The trailing wall 33 may be angled with respect to the flow direction A. Generally, the angle at which the trailing wall 33 is not significant and may be any angle. For example, in one embodiment, the trailing wall 33 is angled a small amount which causes the trailing wall 33 to gradually taper back to the width of the microfluidic channel 16. In yet another alternative, there is no trailing wall 33 and the expansion does not return to the original dimension of the microfluidic channel 16.

In another embodiment as illustrated in FIG. 1J, the expansion region 30 includes a leading wall 31 that is curved. In this regard, the leading wall 31 initially starts a gradually divergence away from the upstream microfluidic channel 16 that increasingly diverges along the length of the leading wall 31. In this embodiment, various tangents taken along different points of the leading wall 31 will have significantly different angles compared to the axis of flow A. For example, near the start of the leading wall 31, the angle $\theta_1$ is low and less than 45°. However, near the end of the leading wall 31, the angle $\theta_2$ is steep and more than 45°. In the case of curved or discontinuous expansion regions 30 like what is illustrated in FIG. 1J, an average angle $\theta_{AVE}$ which represents the average angle with respect to the axis of flow A along the entire length of the leading wall 31 should be greater than 45 ($\theta_{AVE}$>45°).

Figure 1H:
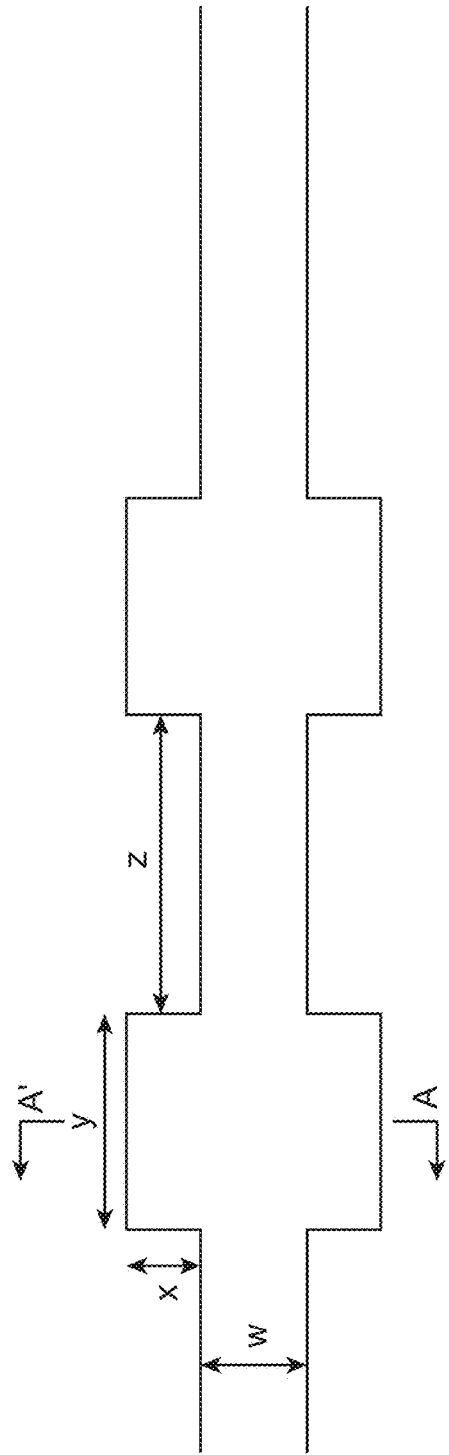
FIG. 1H illustrates a plan view of a microfluidic channel with multiple expansion regions.
Figure 1I:
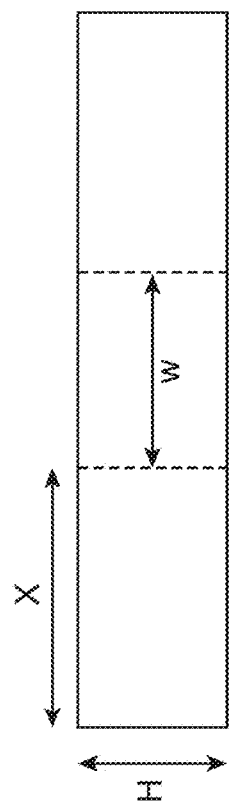
FIG. 1I illustrates a cross-sectional view taken along the line A-A' of FIG. 1H.

FIG. 1H illustrates a plan view of several expansion regions 30 located along a length of a microfluidic channel 16. FIG. 1I illustrates a cross-sectional view taken along the line A-A' of FIG. 1H. Both FIGS. 1H and 1I illustrate various dimensions of the microfluidic channel 16 and expansion regions 30. As stated previously, typical dimensions for the width (w) of microfluidic channel 16 is in the range of 20 µm to 200 µm. Typical dimensions for the height (H) of the microfluidic channel 16 are the range of 20 µm to 500 µm. The expansion region 30 may extend a distance (x) that is in the range between 80 µm and 800 µm but should be at least 80 µm. The expansion region 30 may extend a distance (y) that is in the range of 200 µm to 2 mm. Adjacent expansion regions 30 may be separated by distances (z) typically greater than 20 µm. In some embodiments, there may be a single expansion region 30 such that there is no adjacent expansion region 30. The cross-sectional profile of the microfluidic channel 16 may be substantially rectangular, trapezoidal, or square. The microfabrication process can lead to slightly trapezoidal cross-sections or corners that are slightly rounded. The channels 16 may also have circular or semi-circular cross sections although current fabrication techniques do not produce these geometries. These variations are intended to be covered by the methods and devices described herein.

Figure 3:
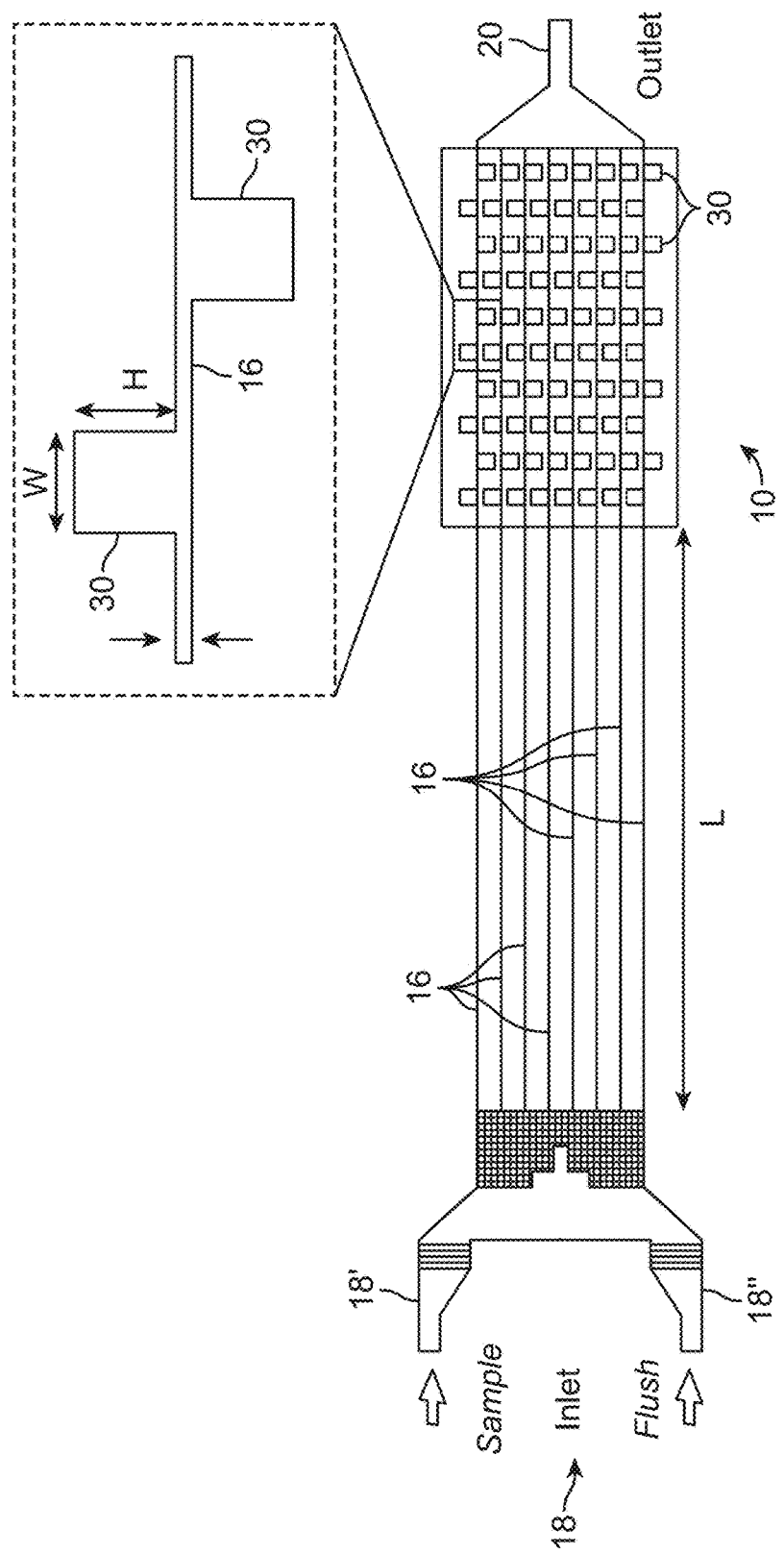
FIG. 3 illustrates another microfluidic device for isolating cells having a parallel configuration.

Referring back to FIG. 1A, the expansion regions 30 may be disposed on opposing sides of the microfluidic channel 16. This enables a single microfluidic channel 16 to have greater capturing capabilities. Moreover, as explained in more detail below, this configuration enables a staggered arrangement of expansion regions 30 when multiple channels 16 are aligned in a parallel configuration. That is to say, adjacent microfluidic channels 16 can be closely packed together because expansion regions 30 are offset from one another and interleave with expansion regions 30 on adjacent microfluidic channels 16 as seen in FIG. 3. Still referring to FIG. 1A, the larger-sized cells 12 are trapped within the expansion regions 30 while the smaller-sized cells 12 are not trapped and continue to flow down the microfluidic channel 16 where they exit via outlet 20. Larger-sized cells 12 (those illustrated in the expansion regions 30) are trapped within a vortex flow that is created within the expansion regions 30. Smaller-sized cells 12, due to their size they are not trapped within the vortex flow and pass out of the expansion regions 30. Thus, smaller-sized cells 12 are not trapped by the vortex in the expansion regions 30 and continue to flow downstream in the microfluidic channel 16.

Figure 2:
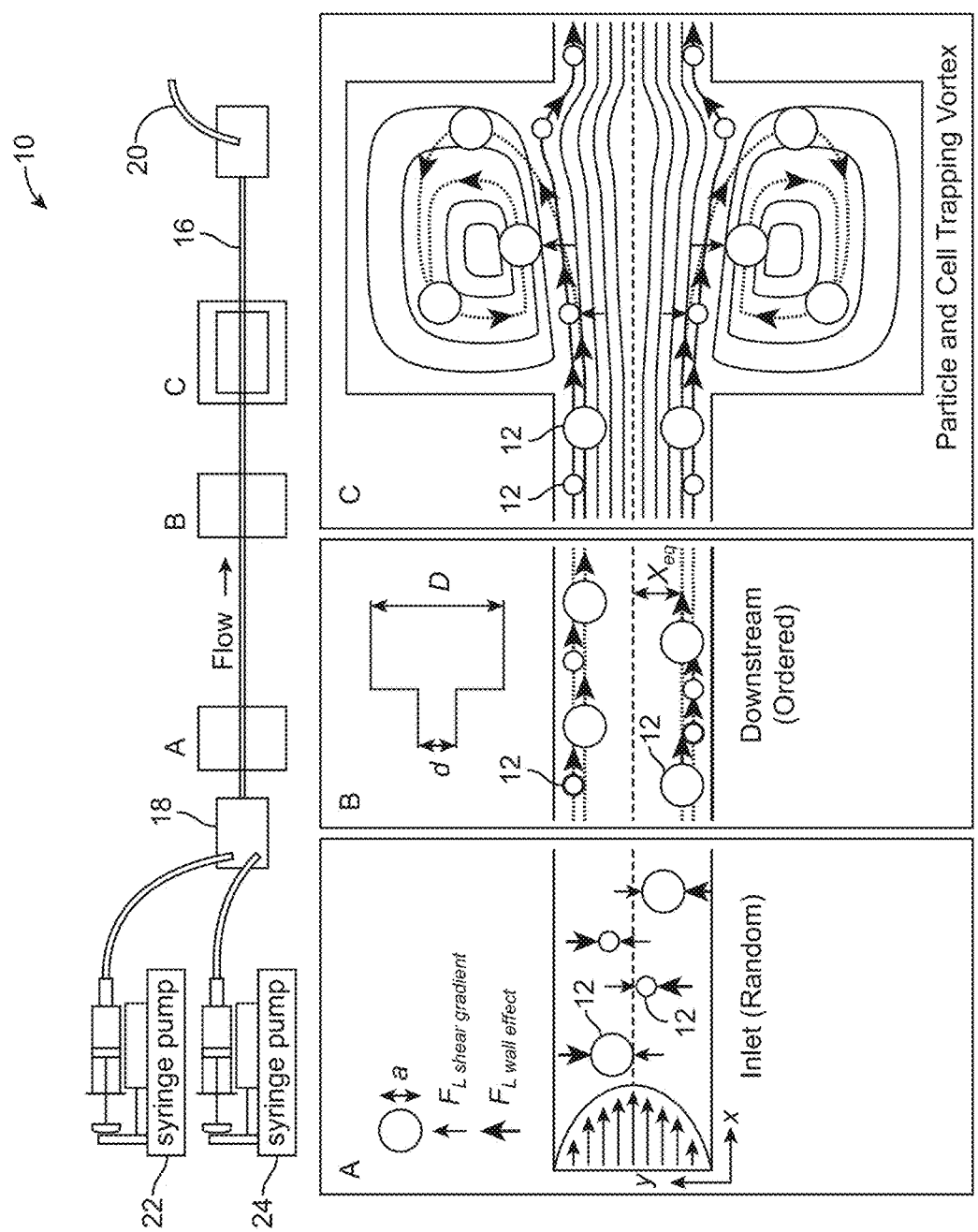
FIG. 2 illustrates a schematic view of a microfluidic device for isolating cells. Also included are graphical representations of forces acting on differing cell sizes at different points along the microfluidic device.

FIG. 2 illustrates a microfluidic device 10 for isolating cells 12 from a heterogeneous solution containing cells 12 of different sizes as well as corresponding flows within the microfluidic channel 16 and expansion regions 30. FIG. 2 illustrates magnified views of three regions of the microfluidic channel 16 and expansion regions 30 as identified by views A, B, and C. As seen in view A, a heterogeneous population of different sized cells 12 is pumped into the device via one of the syringe pumps 22, 24. The other syringe pump may contain a wash or other solution such as PBS. Initially, as seen in view A, the cells 12 are randomly dispersed is the y-direction. The cells 12 experience two counteracting forces—a shear gradient lift force ($F_L$ shear gradient) that acts on the cells 12 to move the same toward the walls of the microfluidic channel 16 and a wall effect lift force ($F_L$ wall effect) that repels cells 12 away from the walls of the microfluidic channel 16.

By using a straight microfluidic channel 16 with a rectangular cross-section, the dynamic equilibrium positions of the flowing cells 12 results in a dynamic lateral equilibrium position $X_{eq}$ and uniform cell velocities as illustrated in view B of FIG. 2. Here, $X_{eq}$ is defined as the distance between the center of cells 12 and the wall of the microfluidic channel 16. As the cells 12 progress to the expansion regions 30 (in FIG. 2 there are two (2) opposing expansion regions 30), the larger cells 12 experiencing a larger $F_L$ shear gradient are pushed toward the vortex center and trapped, whereas the smaller cells 12 are flushed out of the expansion regions 30 and into the channel where they continue the downstream flow to the outlet 20. Generally the $F_L$ shear gradient force scales with the cube of the cell diameter (a), causing larger cells 12 to experience a larger $F_L$ shear gradient force. Size-dependent lateral migration drives cells 12 across streamlines past the detached boundary (separatrix) toward the vortex core where the cells 12 remain isolated and orbiting in the vortex. This enables size-selective trapping, as below a size cutoff, cells do not migrate at a sufficient rate to pass the separatrix and remain in focused streams, flowing out of the outlet 20.

FIG. 3 illustrates another embodiment of a microfluidic device 10 for isolating cells 12 that includes a plurality of channels 16 coupled to an inlet 18 and an outlet 20. FIG. 3 illustrates eight (8) separate channels 16 that arranged generally parallel to one another. Each microfluidic channel 16 has ten (10) separate expansion regions 30. Of course, it should be understood that any number of channels 16 may be used. The same applies with respect to the number of separate expansion regions 30 along a single microfluidic channel 16. Spacing between adjacent expansion regions 30 along a single microfluidic channel 16 may vary but 1 mm spacing has been found to work. Additional channels 16 may be added to create a massively parallel device 10. The channels 16 are straight with expansion regions 30 on adjacent channels 16 being staggered with respect to one other. This design enables adjacent channels 16 to be placed close to one another, thereby reducing the overall footprint of the microfluidic device 10. While FIG. 3 illustrates an array of channels 16 in a two-dimensional layout it should be understood that the array of channels 16 could also be configured in a three-dimensional layout. The three-dimensional configuration would allow even more throughput.

In the device of FIG. 3, the microfluidic channel 16 is a rectangular high-aspect ratio channel with a width of 50 μm and a height of 70 μm. The inlet 18 includes a first inlet 18' for the sample containing the cells 12 and a second inlet 18" that contains PBS or other wash solution. The duel inlet 18', 18" arrangement allows for easy and rapid solution exchange within the microfluidic device 10, providing, for example, a means to flush un-trapped cells 12 and to enhance the final enrichment ratio and the purity of the collected samples. The length of the microfluidic device 10 was several centimeters long. The expansion regions 30 were placed in an alternating pattern in order to place the maximum number of expansion regions 30 in a given compact footprint. In the device of FIG. 3, the expansion regions were squares having dimensions of 400 μm×400 μm.

Once the cells 12 are trapped within the expansion regions 30, the cells 12 may be released from the expansion regions 30 by allowing the vortices to reduce in size and ultimately dissipate. This can be accomplished by lowering the input flow rate (e.g., reduce flow rate(s) of pumps 22, 24). The reduced flow rate reduced the vortex size allowing the cells 12 trapped therein to be released into the flow of the microfluidic channel 16 and carried out the outlet 20 of the device. A flow rate of around 4 ml/minute has been found to work best with the device of FIG. 3. Alternatively, the flow rate may be rapidly decreased to substantially zero to stop the flow of fluid through the microfluidic device 10. In this alternative, the cells 12 can be collected on-chip rather than off-chip.

Example 1—Enrichment of Rare Cancer Cells from Blood

The microfluidic device 10 of FIG. 3 was applied to separating and concentrating cancer cells (diameter of 20 micrometers) from normal human blood cells (diameters range from 2 to 15 micrometers) to demonstrate utility for size-based enrichment and concentration in a high-throughput manner. Enriching and concentrating cancer cells from blood is particularly important for clinical diagnostics as circulating tumor cells (CTCs) can provide real-time information on patient status and monitoring of cancer therapies. Isolating viable CTCs from blood in a quick, effective and label-free approach remains a significant technical challenge—CTCs are rare events at rates as low as one cell per one billion blood cells. While current strategies focus on enumeration of CTCs for diagnostics, there is a critical need for gathering larger sample sizes of viable CTCs for research purposes. This requires processing large blood volumes with higher throughputs and enriching target cells without the attachment to modified substrates or magnetic beads, providing an advantage for individually selecting captured cells for further analysis or culture.

This device 10 addresses the need for rare cell enrichment with a massively parallel device that processes liquid volumes in the mL/min range, enriches target cells through size and density-based separation, and releases captured cells into a smaller concentrated volume. To demonstrate rare cell enrichment, fluorescently-labeled breast cancer cells (MCF-7) spiked into diluted human blood was injected into a device 10 similar to that illustrated in FIG. 3 at 4.4 mL/min rate. MCF7 breast cancer cells were cultured in media containing DMEM supplemented with 10% FBS, 1% bovine insulin, and 1% penicillin/streptomycin were trypsinized and resuspended before use. Blood was collected from healthy human volunteers by a trained physician and diluted in PBS to 5-20% for experiments.

At these high flow rates channel deformation was observed in the upstream vortex reservoirs, however trapping is not significantly impacted given that downstream vortex chambers operating closer to ambient pressure remain un-deformed. Higher operational flow rates are instead limited by bond strength.

Figures 4A, 4B:
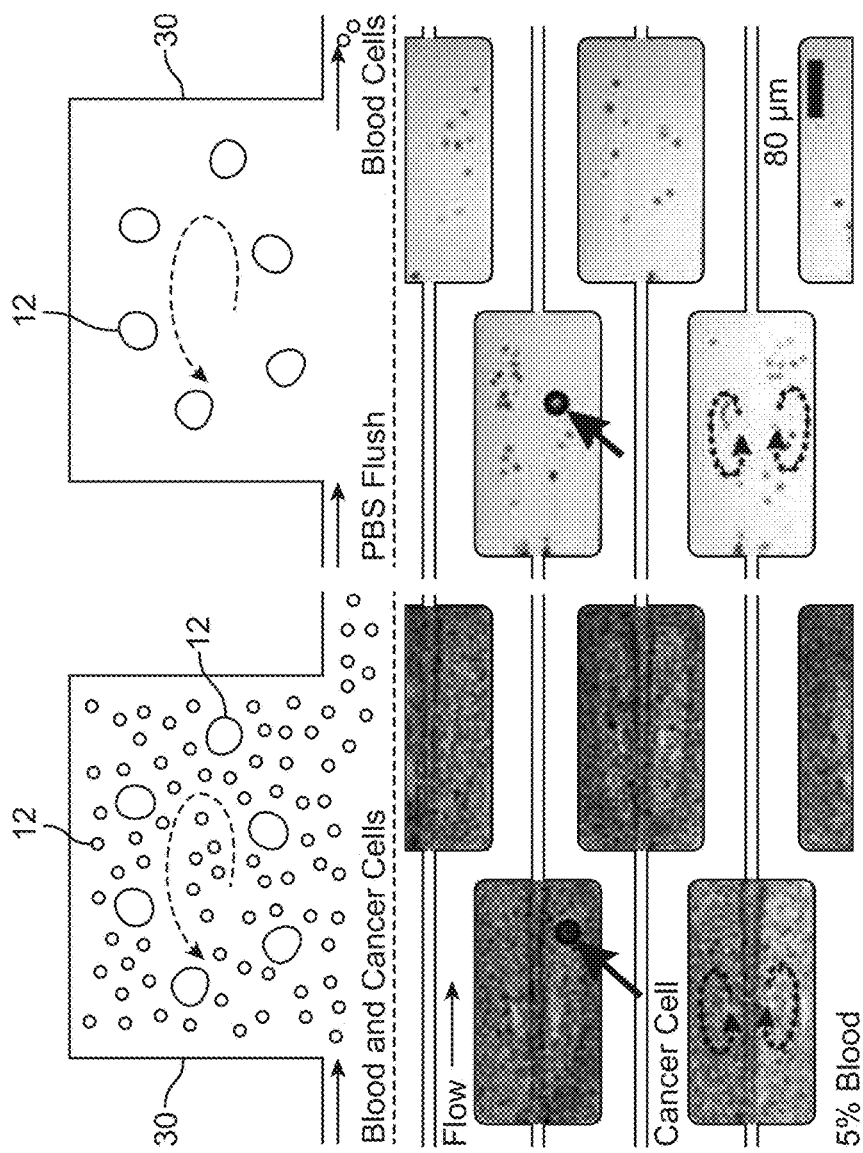
FIG. 4A schematically illustrates blood and cancer cells passing through a portion of the device having an expansion region that traps the larger cancer cells. A corresponding microscope image of a device containing several expansion regions is shown immediately below.
FIG. 4B schematically illustrates a phosphate buffered saline (PBS) flush through the device of FIG. 4A showing evacuation of the red blood cells (RBCs) while cancer cells are retained in the expansion regions. A corresponding microscope image of a device containing several expansion regions is shown immediately below.
Figure 4C:
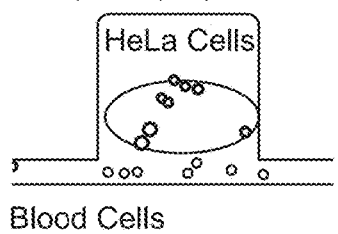
FIGS. 4C-4F illustrates a blood sample spiked with HeLa cells passing through the microfluidic device of FIG. 3 at a Reynolds number (Rc) of 270.
Figure 4D:
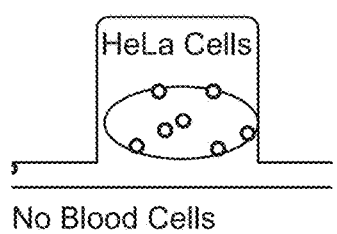
Figure 4E:
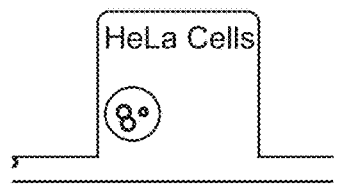
Figure 4F:
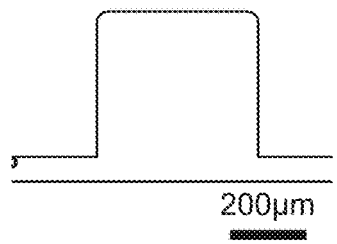

Spiked MCF-7 cells included single cells and 2-4 cell clusters, as clustered cells have been shown to be present at significant levels in clinical samples. Blood and cancer cells were observed to enter and orbit in the vortices during the injection step as illustrated in the schematic view of a single expansion region 30 in the upper panel of FIG. 4A. The lower panel of FIG. 4A illustrates a microscopic image showing a trapped cancer cell along with red blood cells contained in the expansion region 30. Red blood cells were observed to enter vortices even though particles of similar size did not migrate into vortices in experiments with dilute samples. Likely, the high cell concentration induces collisions and hydrodynamic disturbances between cells that lead to cross-stream migration and entrance into vortices.

Additionally, there is a maximum capacity of cells each expansion region 30 can maintain. After the vortex occupies the entire expansion region 30 a maximum of ~40 single MCF7 cells can be maintained over a range of higher flow rates. For most spiking experiments conditions were kept well below this maximum. Once the solution was completely processed, the vortex-trapped cells were "washed" with PBS without disrupting the vortices. This is illustrated in the upper panel of FIG. 4B. The lower panel of FIG. 4B illustrates a microscopic image showing the still trapped cancer cell after a PBS wash solution has been introduced to remove the smaller and denser RBCs. Interestingly, it was observed that blood cells that initially entered the vortex were not stably trapped and quickly exited from the traps and out of the system leaving only the larger stably trapped cancer cells orbiting. Red and white blood cells have both higher density and/or smaller size, and therefore cannot form stable orbits. Washed cells were released into one well of a 96-well-plate for characterization and enumeration.

Figures 5A, 5B, 5C:
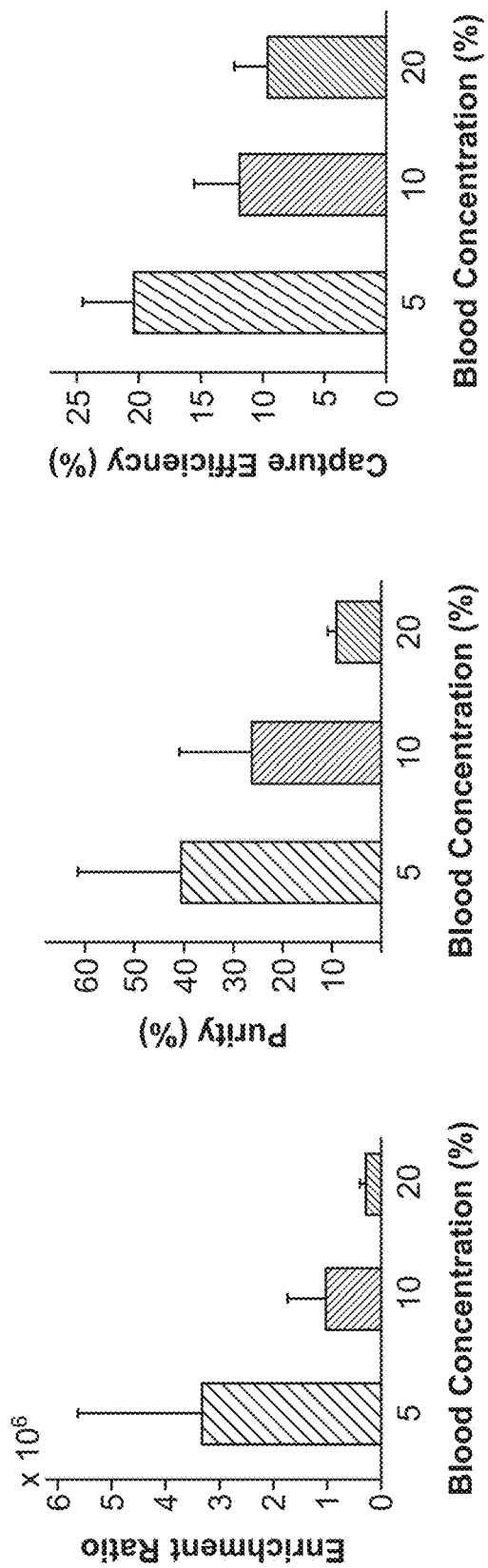
FIG. 5A illustrates a graph of the enrichment ratio (%) achieved with the microfluidic device at various blood concentrations.
FIG. 5B illustrates a graph of the purity (%) achieved with the microfluidic device at various blood concentrations.
FIG. 5C illustrates a graph of the capture efficiency (%) achieved with the microfluidic device at various blood concentrations.

The microfluidic device 10 performs well when quantifying key metrics for target cell concentration, enrichment, and purity. 10 mL volume blood samples (n≥6 samples) of 5% v/v blood (i.e., 0.5 mL whole blood or ~2.5 billion blood cells) spiked with ~500 cancer cells were concentrated to a final volume of less than 200 mL (20-fold volumetric concentration) with relatively little blood cell contamination in <3 min. This corresponds to an enrichment ratio (the ratio of target cancer cells to contaminant blood cells in the output divided by the same ratio in the input solution) of 3.4 million as seen in FIG. 5A. This high level of enrichment leads to high purity of the cancer cells in the 200 mL final volume: ~40% as seen in FIG. 5B (an average of 102±21 cancer cells, and 221±155 blood cells). Blood samples without spiked cancer cells (n=3) that were processed with the microfluidic device 10 and samples were collected in the well and were found to have 772±283 red blood cells and 4±1 CD45+ white blood cells, which is similar to the amount of blood cell contaminants found in the microwells using spiked blood samples. The level of enrichment achieved is comparable to molecular affinity-based and filter-based approaches for target cell separation which have reported enrichments from 1 million to 10 million. The purity of the processed sample is high when compared to affinity-based approaches which report purities of spiked cancer cells of 9.2 to 14.0%. Reducing the dilution of blood in processed samples leads to increases in cell-processing throughput, but also results in reduced capture efficiency of spiked cells. As seen in FIG. 5C, 10 to 20% of the spiked cancer cells were recovered, with decreasing capture efficiency with increasing blood concentrations. Higher blood concentrations lead to higher fluid viscosities which modify the fluid vortex size and position, resulting in lower trapping efficiency.

This relatively low capture efficiency at higher blood concentrations suggests that in order for this technique to be useful in isolating ultra-rare cells occurring at 1-10 cells/mL, a large volume of blood must be processed (10 mL or more). However, the high throughput of the microfluidic device 10 described herein (~5 mL/min of diluted blood for a 2 cm² chip) indicates that operation on large volumes in a reasonable time period (<30 min) is achievable.

Cells captured in the microfluidic device 10 maintained high levels of viability. No significant changes were observed in cell viability (90.1% vs. 90.3% initial) after injecting cells through the device as determined by a fluorescent live/dead assay. Viable cells may be important for some sample preparation applications. Cells captured and released from the microfluidic device 10 are available for standard molecular assays such as immunostaining. To this end, unlabeled spiked blood samples were enriched with the microfluidic device 10. Cancer cells were then released and labeled in a microwell. Cancer cells stained positive for Cytokeratin-PE and DAPI and negative for CD45. This ability to enrich on one device but transfer cells in a small volume for further processing offers significant advantages for rare single cell analysis.

Figure 4G:
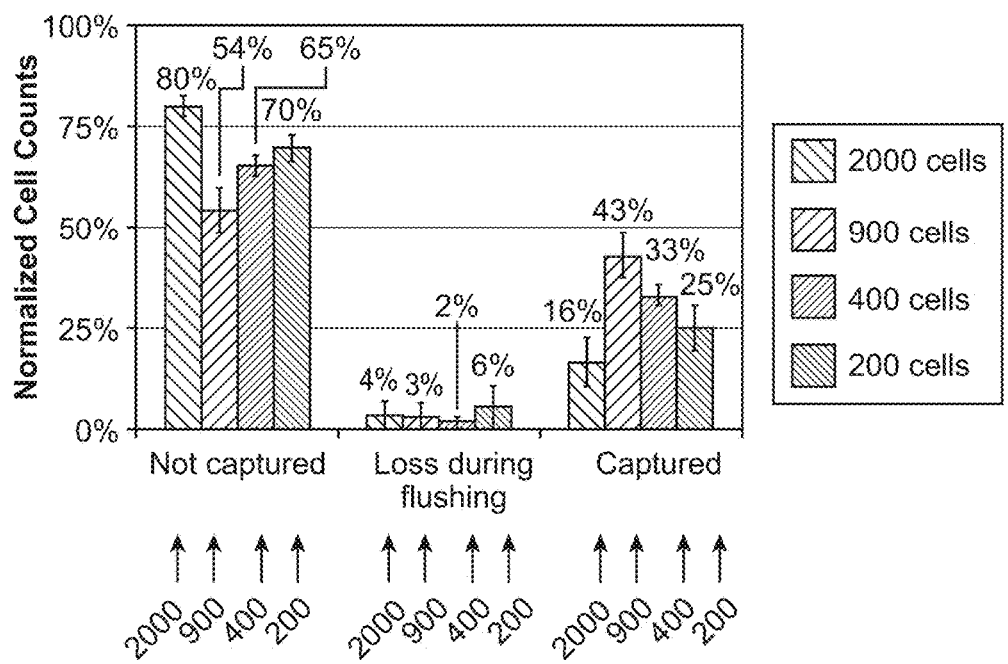
FIG. 4G illustrates a comparison of the capturing efficiency of the microfluidic device as a function of cell concentration.

FIGS. 4C-4F illustrate the results of similar enrichment of a blood sample spiked with HeLa cells using the microfluidic device 10 of FIG. 3 at a Reynolds number (Rc) of 270. The microfluidic device 10 is flushed with PBS wash once the HeLa cells were captured in the expansion regions 30. The trapped HeLa cells were released from the expansion regions 30 by reducing the flow rate to $R_c$=5. FIG. 4G illustrates a comparison of the capturing efficiency of the microfluidic device 10 as a function of cell concentration. The number of cells indicates the number of spiked HeLa cells processed through the microfluidic device 10.

Example 2—Cell Labeling and Solution Exchange

The microfluidic device 10 was also used to effectively label cells for specific molecular markers. In traditional centrifugation, cell samples are labeled for specific markers through a series of labeling and washing steps. This includes incubating the cells with labeling reagents in a centrifuge tube, concentrating the cells into a pellet with a benchtop centrifuge, removing the supernatant layer containing unbound labeling reagents through manual aspiration, and manually resuspending the cells in a new medium. These operations were performed within the microfluidic device 10 by trapping the cells within fluid vortices and sequentially exposing trapped orbiting cells to labeling reagents, followed by a PBS wash solution. Labeled cells were then released within a small volume into a collection vial by reducing flow.

FIGS. 6A-6D illustrate, respectively, the trapping (FIG. 6A), first solution exchange (FIG. 6B), reaction (FIG. 6C), and second solution exchange (FIG. 6D). FIGS. 6E-6H illustrate, respectively, microscope images corresponding to FIGS. 6A-6D of actual MCF7 cells incubated with biotinylated EpCAM that were injected into the microfluidic device 10. As seen in FIG. 6E, cells are trapped in the vortex, undergoing a constant rotating and orbiting motion. FIG. 6F illustrates the first solution exchange with streptavidin-coated microspheres. The streptavidin-coated microspheres enter the expansion region 30. FIG. 6G illustrates the continuous reaction of the streptavidin-coated microspheres with the MCF7 cells. FIG. 6H illustrates a solution exchange with a second solution (i.e., PBS wash). The PBS wash removes unbound microspheres (arrow A). After the wash is complete the cells are released from vortex traps by lowering the flow rate through the microfluidic device 10 wherein the cells are collected into a 96-well-plate for characterization. Arrows B in FIG. 6H point to particles that are increasingly bound to the cell over 2 minutes.

The ability to hold cells stably in place within fluid vortices allows for multiple solution exchanges with labeling agents and wash solutions in a format that can be automated. Each addition of a new solution takes approximately 100 ms for complete exchange. For the same labeling reaction a traditional centrifuge-based process requires six (6) centrifugation steps that includes three (3) washing steps and requires >30 minutes of sample preparation time (this excludes the incubation time with labeling reagents). Each centrifugation and wash step can potentially result in a loss of a small proportion of cells and requires between 5-10 min.

Fast labeling is aided by cells that rotate and orbit in the fluid vortex such that they are exposed to a constantly refreshed milieu of molecular labels. In other words, strong convection of labeling reagents in the vortex leads to a very small depleted region of reagents near the cell surface and a strong gradient driving more reagents to the cell surface. This fast labeling was observed by examining the binding of streptavidin-coated microspheres to biotinylated anti-EpCAM antibodies on the cell surface (FIGS. 6A-6H). It was found that the cells in the microfluidic device 10 accumulated the same number of microbeads in 5 minutes that cells prepared with the standard protocol accumulated in 30 minutes. Further, after 30 minutes, cells labeled with the microfluidic device 10 on average had twice the number of microbeads bound per cell compared to standard methods.

Example 3—Sequential Operations: Rare Cell Enrichment Followed by Labeling

Figure 7:
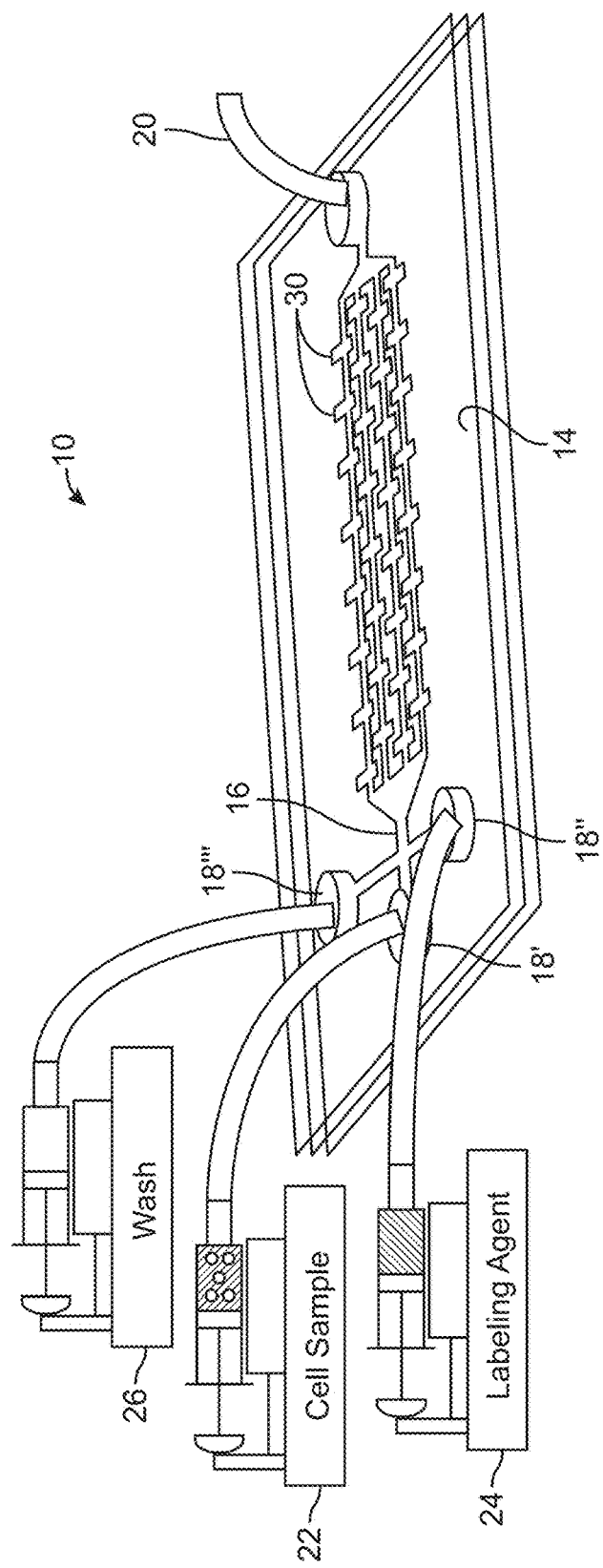
FIG. 7 illustrates a microfluidic device according to another embodiment that includes three inlets coupled to three different solutions: cell sample, labeling agent, and wash.
Figure 8:
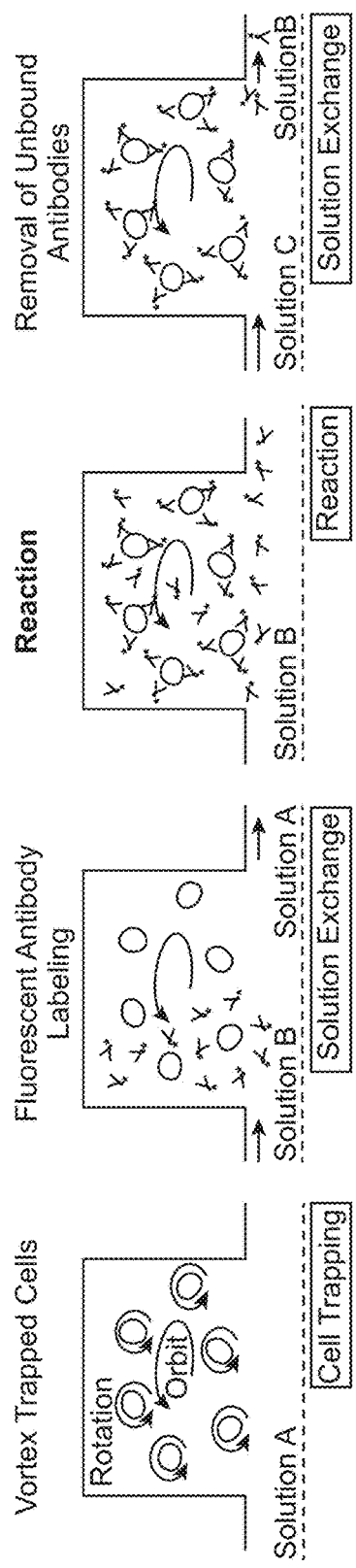
FIGS. 8A-8D illustrate the sequential steps of trapping, fluorescent solution exchange, reaction, and wash conducted on the device of FIG. 7.
Figure 9:
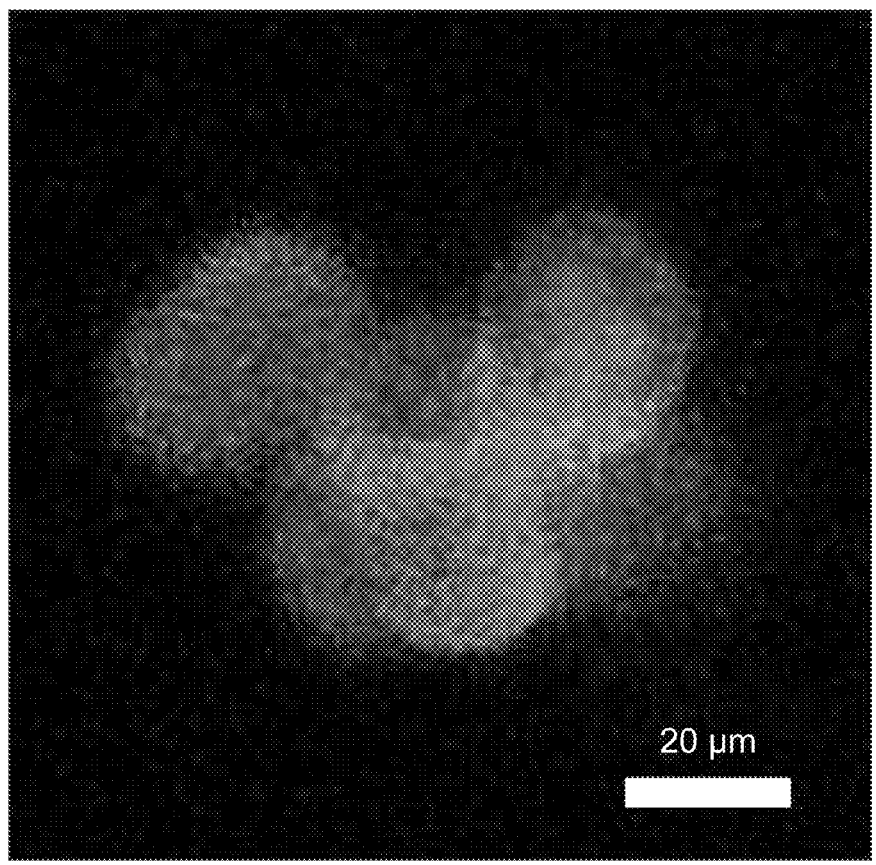
FIG. 9 illustrates a fluorescent image of a cluster of cells that was sequentially trapped inside the fluid vortex, fixed with paraformaldehyde, permeabilized, and labeled with anti-Cytokeratin-PE & DAPI.
Figure 10:
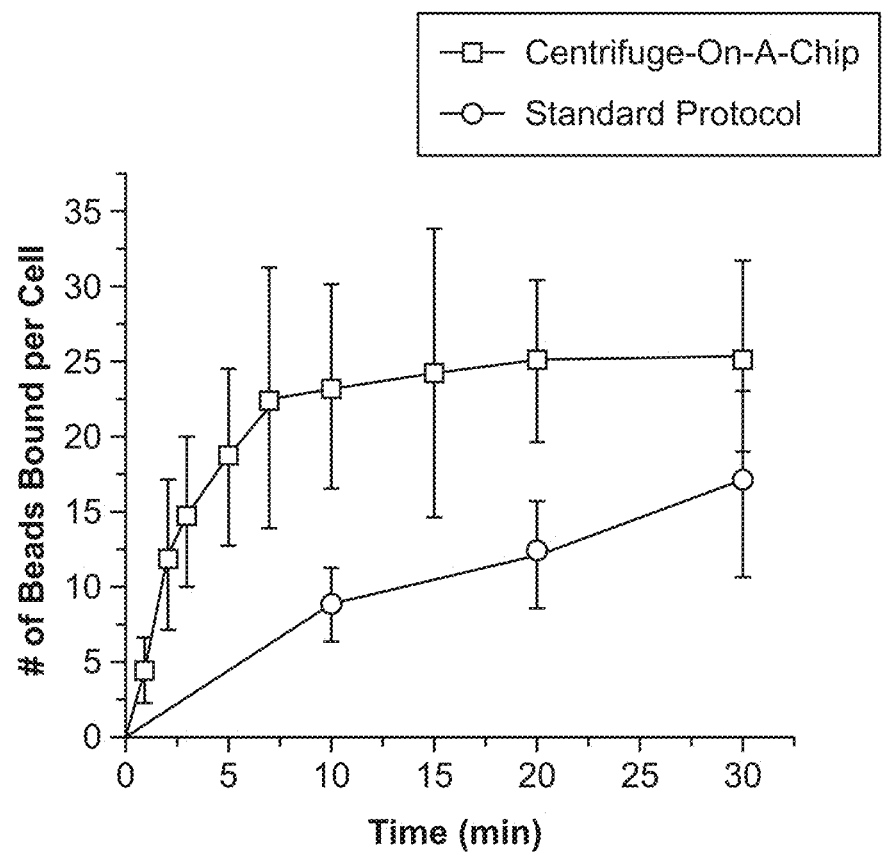
FIG. 10 illustrates a graph of the number of streptavidin-coated microbeads bound per cell (MCF7 cells covered with biotinylated anti-EpCAM) as a function of time for both the microfluidic device and standard centrifugation.
Figure 11:
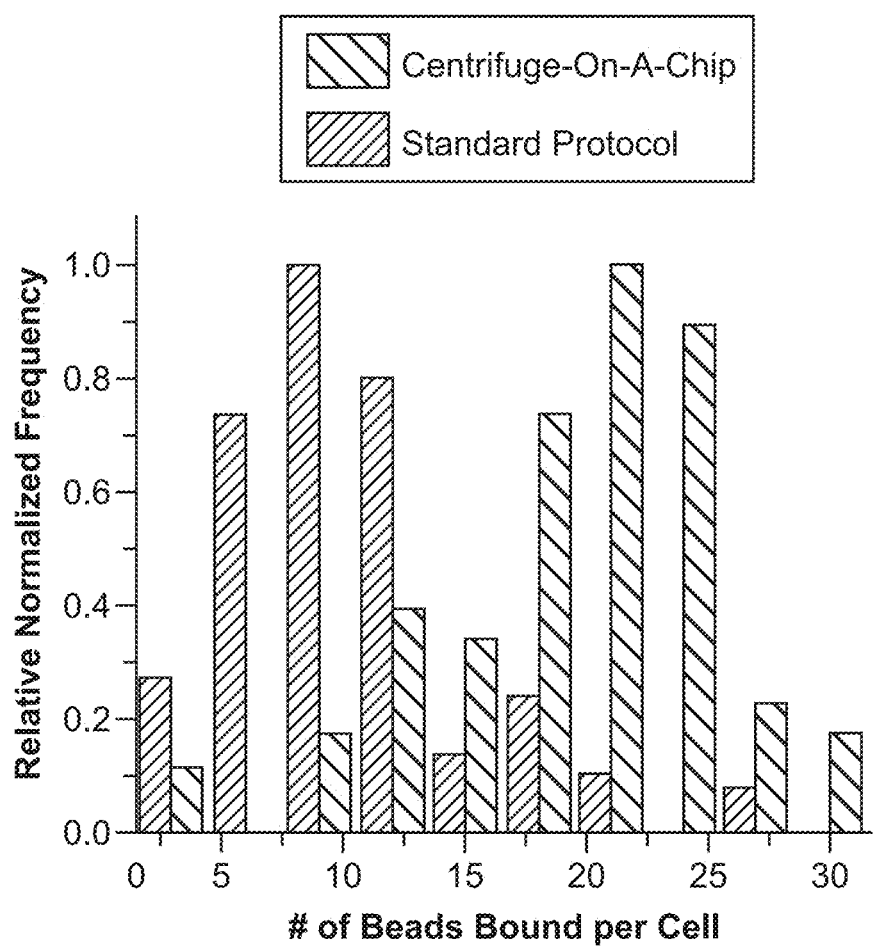
FIG. 11 illustrates a graph of the relative normalized frequency as a function of number of beads bound per cell for both the microfluidic device and standard centrifugation.

Multiple sequential sample preparation steps enabled by a centrifuge (e.g., trapping fluorescent solution exchange, reaction, and wash) were successfully conducted using the microfluidic device 10 illustrated in FIG. 7. In this embodiment, the microfluidic device 10 included three inlets 18', 18", and 18'". One inlet 18' was coupled a syringe pump 22 that was used to deliver the cell sample. The second syringe pump 24 was used to deliver the fluorescent agent. The third syringe pump 26 is used to deliver wash (PBS). Size-based trapping of cancer cells from blood, sequential fluorescent labeling, and analysis of released cells were conducted in <1 hour. Diluted human blood (10 mL) spiked with cancer cells was injected into the microfluidic device 10 for ~3 min to enrich the cancer cells. Trapped cells were sequentially prepared with a fixation agent (paraformaldehyde) and permeabilization agent and stained with fluorescent antibodies (anti-Cytokeratin-PE & DAPI) for 20 min. The sequence of trapping, first solution exchange, reaction, and second solution exchange is seen in FIGS. 8A-8D. Cells were then washed with PBS for <1 min, and collected into a 96-well-plate for characterization. Collected cells labeled positive for cytokeratin and DAPI, indicating the success of sequential sample preparation as illustrated in FIG. 9 which shows a fluorescent image of a cluster of cells that was sequentially trapped inside the fluid vortex, fixed with paraformaldehyde, permeabilized, and labeled with anti-Cytokeratin-PE & DAPI. As seen in FIG. 1A0, MCF7 cells covered with biotinylated anti-EpCAM are coated with streptavidin conjugated microbeads in <5 minutes at the same level as a standard off-chip protocol after 30 minutes. FIG. 1A1 illustrates uniform labeling with microbeads over the cell population after 30 minutes. Further, the microfluidic device 10 (centrifuge-on-chip) results in a larger number of beads bound per cell. The results above demonstrate a complete route to automation of all of the sample preparation processes required for cell analysis in a single simple platform.

The devices 10 and methods described herein are useful for inexpensive and rapid circulating tumor cell (CTC) analysis. CTC detection and enumeration is a valuable and promising diagnostic tool for monitoring breast cancer status and outcome. CTCs are tumor-derived cells that spread via the bloodstream and can reflect the aggressiveness of a tumor. CTCs are rare events at rates as low as one cell per one billion cells. CTC isolation thus presents a significant technological challenge. The devices 10 and methods described herein can exploit the cell size difference between CTCs and blood cells (CTCs are 2-4 times larger than RBCs) to isolate viable CTCs from whole blood in a label-free manner. Other potential applications of the devices 10 and methods include prenatal testing that involves the isolation of fetal cells from maternal blood cells. Fetal cells of interest can be isolated without labeling or external bulk machines.

While the microfluidic device 10 has particular application for isolating CTCs, other applications include concentrating cells 12 obtained from a sample. For example, cells 12 of interest having a size that enables trapping within expansion regions 30 can be captured then released into a sample in concentrated form. For example, cells 12 contained in a biological source of fluid like urine, pleural fluid, and peritoneal washes can be run through the microfluidic device 10 to concentrate cells 12 contained therein. In this regard, the microfluidic device 10 is well suited for concentrating cells 12. For example, on a volumetric basis, the microfluidic device 10 can concentrate cells 12 more than ten (10) or twenty (20) times the concentration of the cells 12 in the initial solution.

While embodiments have been shown and described, various modifications may be made without departing from the scope of the inventive concepts disclosed herein. For example, while several embodiments have been described herein it should be appreciated that various aspects or elements are interchangeable with other separately embodiments. The invention(s), therefore, should not be limited, except to the following claims, and their equivalents.

What is claimed is:

1. A method of exchanging solution around isolated cells comprising: providing a microfluidic device having at least one microfluidic channel coupled to a first inlet and one or more additional inlets, and an outlet, the at least one microfluidic channel comprising a plurality of expansion regions disposed along the length thereof, the plurality of expansion regions comprising an abrupt increase in a cross-sectional dimension of the at least one microfluidic channel followed by an abrupt decrease in the cross-sectional dimension of the at least one microfluidic channel, wherein the plurality of expansion regions are configured to generate vortices within each expansion region in response to fluid flow;

flowing a first solution containing a population of cells into the first inlet;

trapping at least a portion of the cells within the vortices created within the plurality of expansion regions;

flowing one or more solutions different from the first solution into the one or more additional inlets while continuously maintaining the vortices containing the trapped cells; and reducing fluid flow through the microfluidic device to release the trapped cells from the plurality of expansion regions after exposure to the one or more solutions different from the first solution.

2. The method of claim 1, wherein releasing the trapped cells comprises reducing fluid flow through the microfluidic device to substantially zero.

3. The method of claim 1, wherein the one or more solutions comprises a solution containing a reagent selected from the group consisting of a fluorescent label, antibody, nucleic acid dye, fluorogenic substrate, fixation reagent, or permeabilization reagent.

4. The method of claim 1, further comprising flowing a wash solution into the one or more additional inlets after flowing the one or more solutions and before releasing the trapped cells.

5. The method of claim 1, further comprising maintaining the vortices so that the volumetric concentration of cells trapped in the plurality of expansion regions is more than 10 times greater than the volumetric concentration of the cells in the first solution.

6. The method of claim 1, further comprising pumping the first solution into the first inlet with a first pump and pumping the one or more solutions different from the first solution into the one or more additional inlets with a second pump.

7. The method of claim 6, further comprising reducing the flow rate of the first pump or the second pump to release the trapped cells.

8. The method of claim 1, further comprising flowing a first different solution for about 100 ms followed by a second different solution for about 100 ms.

9. The method of claim 8, the first different solution comprises a label and the second different solution comprises a wash solution.

* * * * *